United States Patent
Shennib

(10) Patent No.: US 9,326,706 B2
(45) Date of Patent: May 3, 2016

(54) HEARING PROFILE TEST SYSTEM AND METHOD

(71) Applicant: iHear Medical, Inc., San Leandro, CA (US)

(72) Inventor: Adnan Shennib, Oakland, CA (US)

(73) Assignee: iHear Medical, Inc., San Leandro, CA (US)

( * ) Notice: Subject to any disclaimer, the term of this patent is extended or adjusted under 35 U.S.C. 154(b) by 160 days.

(21) Appl. No.: 14/011,620

(22) Filed: Aug. 27, 2013

(65) Prior Publication Data

US 2015/0025413 A1    Jan. 22, 2015

Related U.S. Application Data

(60) Provisional application No. 61/847,026, filed on Jul. 16, 2013.

(51) Int. Cl.
*A61B 5/12* (2006.01)
*A61B 5/00* (2006.01)
*H04R 25/00* (2006.01)

(52) U.S. Cl.
CPC ............... *A61B 5/123* (2013.01); *A61B 5/6898* (2013.01); *A61B 5/7415* (2013.01); *A61B 5/7435* (2013.01);
(Continued)

(58) Field of Classification Search
CPC ...... A61B 5/123; A61B 5/121; A61B 5/0022; A61B 5/7405; A61B 5/7415; A61B 5/7435; H04R 25/30; H04R 25/305
USPC ...................................... 600/559; 381/58–60
See application file for complete search history.

(56) References Cited

U.S. PATENT DOCUMENTS

| 4,759,070 A | 7/1988 | Voroba |
| 5,197,332 A | 3/1993 | Shennib |

(Continued)

FOREIGN PATENT DOCUMENTS

| JP | 2008109594 A | 5/2008 |
| KR | 1020050114861 A | 12/2005 |

(Continued)

OTHER PUBLICATIONS

Internet Archive, Basic Guide to in Ear Canalphones, Head-Fi.org, Jul. 1, 2012. Retrieved from <https://web.archive.org/web/20120701013243/http://www.head-fi.org/a/basic-guide-to-in-ear-canalphones> on Apr. 14, 2015.*

(Continued)

*Primary Examiner* — Devin Henson
*Assistant Examiner* — David J McCrosky
(74) *Attorney, Agent, or Firm* — Dorsey & Whitney LLP

(57) ABSTRACT

Examples of systems and methods for profiling the hearing ability of a consumer are disclosed. One example includes a personal computer and a handheld device configured to produce calibrated acoustic output at suprathreshold levels above 20 db HL, and at step levels of 10-20 decibels, and presented test frequency bands across an audiometric frequency range from 400 to 8000Hz. The consumer's minimal audibility levels are registered, and a hearing profile score is presented to indicate hearing ability and hearing aid candidacy. In some embodiments, band-limited natural sounds are presented. Systems and methods disclosed herein, with considerations for noise present in the consumer's environment, allow for rapid calibrated hearing profiling, using a standard personal computer and minimal hardware, thus particularly suited for self-testing outside clinical environments such as at home or the office.

38 Claims, 13 Drawing Sheets

(52) U.S. Cl.
CPC ............ *A61B 5/7465* (2013.01); *A61B 5/7475* (2013.01); *A61B 2560/0431* (2013.01); *H04R 25/305* (2013.01)

(56) References Cited

U.S. PATENT DOCUMENTS

| | | | |
|---|---|---|---|
| 5,327,500 | A | 7/1994 | Campbell |
| 5,553,152 | A | 9/1996 | Newton |
| 5,645,074 | A | 7/1997 | Shennib et al. |
| 5,659,621 | A | 8/1997 | Newton |
| 5,701,348 | A | 12/1997 | Shennib et al. |
| 5,785,661 | A | 7/1998 | Shennib et al. |
| 5,928,160 | A * | 7/1999 | Clark .................. A61B 5/12 600/559 |
| 6,137,889 | A | 10/2000 | Shennib et al. |
| 6,212,283 | B1 | 4/2001 | Fletcher et al. |
| 6,319,207 | B1 | 11/2001 | Naidoo |
| 6,359,993 | B2 | 3/2002 | Brimhall |
| 6,367,578 | B1 | 4/2002 | Shoemaker |
| 6,379,314 | B1 | 4/2002 | Horn |
| 6,428,485 | B1 | 8/2002 | Rho |
| 6,447,461 | B1 | 9/2002 | Eldon |
| 6,473,513 | B1 | 10/2002 | Shennib et al. |
| 6,522,988 | B1 | 2/2003 | Hou |
| 6,546,108 | B1 | 4/2003 | Shennib et al. |
| 6,674,862 | B1 | 1/2004 | Magilen |
| 6,724,902 | B1 | 4/2004 | Shennib et al. |
| 6,840,908 | B2 | 1/2005 | Edwards et al. |
| 6,937,735 | B2 | 8/2005 | DeRoo et al. |
| 6,940,988 | B1 | 9/2005 | Shennib et al. |
| 6,978,155 | B2 | 12/2005 | Berg |
| 7,016,511 | B1 | 3/2006 | Shennib |
| 7,037,274 | B2 | 5/2006 | Thoraton et al. |
| 7,113,611 | B2 | 9/2006 | Leedom et al. |
| 7,215,789 | B2 | 5/2007 | Shennib et al. |
| 7,260,232 | B2 | 8/2007 | Shennib |
| 7,298,857 | B2 | 11/2007 | Shennib et al. |
| 7,310,426 | B2 | 12/2007 | Shennib et al. |
| 7,321,663 | B2 | 1/2008 | Olsen |
| 7,403,629 | B1 | 7/2008 | Aceti et al. |
| 7,424,123 | B2 | 9/2008 | Shennib et al. |
| 7,424,124 | B2 | 9/2008 | Shennib et al. |
| 7,580,537 | B2 | 8/2009 | Urso et al. |
| 7,664,282 | B2 | 2/2010 | Urso et al. |
| 7,854,704 | B2 | 12/2010 | Givens et al. |
| 7,945,065 | B2 | 5/2011 | Menzl et al. |
| 8,073,170 | B2 | 12/2011 | Kondo et al. |
| 8,077,890 | B2 | 12/2011 | Schumaier |
| 8,155,361 | B2 | 4/2012 | Schindler |
| 8,184,842 | B2 | 5/2012 | Howard et al. |
| 8,243,972 | B2 | 8/2012 | Latzel |
| 8,284,968 | B2 | 10/2012 | Schumaier |
| 8,287,462 | B2 | 10/2012 | Givens et al. |
| 8,379,871 | B2 | 2/2013 | Michael et al. |
| 8,396,237 | B2 | 3/2013 | Schumaier |
| 8,447,042 | B2 | 5/2013 | Gurin |
| 8,467,556 | B2 | 6/2013 | Shennib et al. |
| 8,503,703 | B2 | 8/2013 | Eaton et al. |
| 2001/0008560 | A1 | 7/2001 | Stonikas et al. |
| 2001/0051775 | A1 * | 12/2001 | Rho .................. A61B 5/12 600/559 |
| 2002/0027996 | A1 | 3/2002 | Leedom et al. |
| 2002/0085728 | A1 | 7/2002 | Shennib et al. |
| 2003/0007647 | A1 | 1/2003 | Nielsen et al. |
| 2003/0078515 | A1 | 4/2003 | Menzel et al. |
| 2005/0094822 | A1 | 5/2005 | Swartz |
| 2005/0226447 | A1 | 10/2005 | Miller, III |
| 2005/0245991 | A1 | 11/2005 | Faltys et al. |
| 2005/0259840 | A1 | 11/2005 | Gable et al. |
| 2005/0283263 | A1 | 12/2005 | Eaton et al. |
| 2006/0291683 | A1 | 12/2006 | Urso et al. |
| 2007/0076909 | A1 | 4/2007 | Roeck et al. |
| 2007/0237346 | A1 | 10/2007 | Fichtl et al. |
| 2008/0240452 | A1 | 10/2008 | Burrows et al. |
| 2008/0273726 | A1 | 11/2008 | Yoo et al. |
| 2010/0040250 | A1 | 2/2010 | Gebert |
| 2010/0119094 | A1 | 5/2010 | Sjursen et al. |
| 2010/0145411 | A1 | 6/2010 | Spitzer |
| 2010/0191143 | A1 * | 7/2010 | Ganter .................. A61B 5/123 600/559 |
| 2010/0239112 | A1 | 9/2010 | Howard et al. |
| 2010/0268115 | A1 | 10/2010 | Wasden et al. |
| 2010/0284556 | A1 | 11/2010 | Young |
| 2011/0058697 | A1 | 3/2011 | Shennib et al. |
| 2011/0190658 | A1 | 8/2011 | Sohn et al. |
| 2011/0200216 | A1 | 8/2011 | Lee et al. |
| 2012/0051569 | A1 | 3/2012 | Blamey et al. |
| 2012/0130271 | A1 | 5/2012 | Margolis et al. |
| 2012/0177212 | A1 | 7/2012 | Hou et al. |
| 2012/0177235 | A1 | 7/2012 | Solum |
| 2012/0183164 | A1 | 7/2012 | Foo et al. |
| 2012/0183165 | A1 | 7/2012 | Foo et al. |
| 2012/0189140 | A1 | 7/2012 | Hughes |
| 2012/0213393 | A1 | 8/2012 | Foo et al. |
| 2012/0215532 | A1 | 8/2012 | Foo et al. |
| 2012/0302859 | A1 | 11/2012 | Keefe |
| 2013/0177188 | A1 | 7/2013 | Apfel et al. |
| 2013/0243229 | A1 | 9/2013 | Shennib et al. |
| 2015/0023512 | A1 | 1/2015 | Shennib |
| 2015/0023534 | A1 | 1/2015 | Shennib |
| 2015/0023535 | A1 | 1/2015 | Shennib |

FOREIGN PATENT DOCUMENTS

| | | |
|---|---|---|
| WO | 99/07182 | 2/1999 |
| WO | 2010/091480 | 8/2010 |
| WO | 2011128462 A2 | 10/2011 |
| WO | 2015009559 A1 | 1/2015 |
| WO | 2015009561 A1 | 1/2015 |
| WO | 2015009564 A1 | 1/2015 |
| WO | 2015009569 A1 | 1/2015 |

OTHER PUBLICATIONS

Internet Archive, dB HL—Sensitivity to Sound—Clinical Audiograms, AuditoryNeuroscience.com, Apr. 20, 2013. Retrieved from <https://web.archive.org/web/20130420060438/http://www.auditoryneuroscience.com/acoustics/clinical_audiograms> on Apr. 14, 2015.*

Internet Archive, The Audiogram, ASHA.org, Jun. 21, 2012. Retrieved from <https://web.archive.org/web/20120621202942/http://www.asha.org/public/hearing/Audiogram> on Apr. 14, 2015.*

Amlani, et al. "Methods and Applications of the Audibility Index in Hearing Aid Selection and Fitting." Trends in Amplification 6.3 (2002): 81. Retrieved from <http://www.ncbi.nlm.nih.gov/pmc/articles/PMC4168961/> on Apr. 14, 2015.*

Kryter. "Methods for the calculation and use of the articulation index." The Journal of the Acoustical Society of America 34.11 (1962): 1689-1697. Retrieved from <http://dx.doi.org/10.1121/1.1909094> on Aug. 27, 2015.*

Internet Archive, World Health Organization website "Grades of Hearing Impairment". Retrieved from <https://web.archive.org/web/20121024120107/http://www.who.int/pbd/deafness/hearing_impairment_grades/en> on Aug. 27, 2015.*

Sindhusake et al. "Validation of self-reported hearing loss. The Blue Mountains hearing study." International Journal of Epidemiology 30.6 (2001): 1371-1378. Retrieved from <http://ije.oxfordjournals.org/content/30/6/1371.full> on Aug. 27, 2015.*

International Search Report and Written Opinion for PCT/US2014/046350 mailed Nov. 6, 2014.

International Search Report and Written Opinion for PCT/US2014/046316 mailed on Nov. 3, 2014.

International Search Report and Written Opinion for PCT/US2014/046323 mailed on Oct. 10, 2014.

International Search Report and Written Opinion for PCT/US2014/046335.

International Search Report and Written Opinion dated Nov. 3, 2010 for PCT Appl. No. PCT/US2010/048299.

"Lyric User Guide", http://www.phonak.com/content/dam/phonak/b2b/C_M_tools/Hearing_Instruments/Lyric/documents/02-gb/Userguide_Lyric_V8_GB_FINAL_WEB.pdf, Jul. 2010.

(56) References Cited

OTHER PUBLICATIONS

"Methods for Calculation of the Speech Intelligibility Index", American National Standards Institute, Jun. 6, 1997.
"Specification for Audiometers", American National Standards Institute, Nov. 2, 2010.
"User Manual—2011", AMP Personal Audio Amplifiers.
Abrams, "A Patient-adjusted Fine-tuning Approach for Optimizing the Hearing Aid Response", The Hearing Review, pp. 1-8, Mar. 24, 2011.
Asha, "Type, Degree, and Configuration of Hearing Loss", American Speech-Language-Hearing Association; Hearing Association; Audiology Information Series, May 2011, pp. 1-2.
Convery, et al., "A Self-Fitting Hearing Aid: Need and Concept", http://tia.sagepubl.com, Dec. 4, 2011, pp. 1-10.
Franks, "Hearing Measurements", National Institute for Occupational Safety and Health, Jun. 2006, pp. 183-232.
Kiessling, "Hearing aid fitting procedures—state-of-the-art and current issues", Scandinavian Audiology, 2001, 57-59, vol. 30, Suppl 52.
Nhanes, "Audiometry Procedures Manual", National Health and Nutrition Examination Survey, Jan. 2003, pp. 1-105.
Traynor, "Prescriptive Procedures", www.rehab.research.va.gov/mono/ear/traynor.htm, Jan. 1999, pp. 1-16.
World Health Organization, "Deafness and Hearing Loss", www.who.int/mediacentre/factsheets/fs300/en/index.html, Feb. 2013, pp. 1-5.

* cited by examiner

HEARING PROFILE TEST SYSTEM AND METHOD

CROSS-REFERENCE TO RELATED APPLICATIONS

This application claims the benefit under 35 U.S.C. 119 of the earlier filing date of U.S. Provisional Application No. 61/847,026 entitled "HEARING PROFILE TEST SYSTEM AND METHOD," filed Jul. 16, 2013. The aforementioned provisional application is hereby incorporated by reference in its entirety, for any purpose.

TECHNICAL FIELD

Examples described herein relate to methods and systems of hearing testing, particularly for rapidly profiling the hearing ability of a person, and for determining hearing aid candidacy. This application is related to U.S. patent application Ser. No. 12/878,928, titled, "CANAL HEARING DEVICE WITH DISPOSABLE BATTERY MODULE," issued as U.S. Pat. No. 8,467,556, U.S. patent application Ser. No. 13/424,242, titled, "BATTERY MODULE FOR PERPENDICULAR DOCKING INTO A CANAL HEARING DEVICE," issued as U.S. Pat. No. 8,855,345; U.S. patent application Ser. No. 14/011,604, titled, "HEARING AID FITTING SYSTEMS AND METHODS USING SOUND SEGMENTS REPRESENTING RELEVANT SOUNDSCAPE," issued as U.S. Pat. No. 9,031,247; U.S. patent application Ser. No. 14/011,581, titled, "INTERACTIVE HEARING AID FITTING SYSTEM AND METHODS," issued as U.S. Pat. No. 9,107,016, and pending U.S. patent application Ser. No. 14/011,607, titled. "ONLINE HEARING AID FITTING SYSTEM AND METHODS FOR NON-EXPERT USER," filed on Aug. 27, 2013; all of which are incorporated herein by reference in their entirety for any purpose.

BACKGROUND

Pure tone audiometry is the gold standard for hearing assessment. It relies on identifying the threshold of hearing for an individual, generally using tonal sounds generated by instrumentation designed for clinical use by a hearing professional. The instrumentation and accessories for standard hearing tests are generally specialized electro-medical devices for use in a clinical setting. For example, to obtain a valid threshold test and an audiogram report, tests are generally performed in specialized sound-isolated rooms, often referred to as a "sound room," to reduce noise levels present in the environment generally to that below the threshold of normal hearing. The combined cost of a sound room and clinical instrumentation for standard audiogram testing can easily exceed $20,000.

Performing a hearing assessment is generally not practical for lay consumers to self-administer, particularly in their home or office setting. Even in quiet room environments, noise levels typically exceed the maximum level required for accurately determining the threshold of hearing. Another limitation for self-administration of a hearing test at home is the complexity associated with the test procedure, which can be perplexing and time consuming for a lay person.

Current hearing evaluation methods and associated reports are generally designed for administration and interpretation by hearing professionals, such as an audiologist, an otolaryngologist, a hearing aid dispenser, etc. Standard audiogram results are generally of little value to a lay consumer and generally present irrelevant information pertaining to hearing aid candidacy. The audiogram test report, generally considered the standard form for hearing assessment and hearing aid prescription, is technical and not suitable for interpretation by a potential hearing aid consumer. For example, a standard audiogram report generally presents a person's hearing sensitivity for tonal sounds from −10 to 110 dB, inversely displayed, versus test frequencies from 125 to 8000 Hz. The hearing sensitivity for each frequency may also be tabulated in other audiogram forms. However, since these reports were designed mainly for clinical diagnostics and interpretation by a professional, they are generally not useful for a lay consumer, particularly for indicating hearing aid candidacy. Furthermore, determining the hearing ability in certain ranges, such as −10 to +15 dB HL, is generally not relevant to a person's ability to carry on normal conversations. Another limitation is the irrelevance of audiometric tonal sounds, which generally do not represent real life sounds. Another barrier for self-performed hearing assessment is related to the aforementioned cost, complexity and inaccessibility of standard hearing test instruments.

To circumvent some of the limitations of standard hearing evaluation methods, automated, computer-based hearing evaluation methods have been proposed, including self-administered online tests using personal computers. These tests are often inadequate, however, due to their inaccuracy, often caused by audio characteristics of consumer electronics not meeting the standards of audiometric testing. For example, consumer electronics, such as a sound card, may introduce unacceptable total harmonic distortion (THD), unpredictable frequency response, excessive signal noise, and/or excessive cross-over distortion. The sources of adverse audio characteristics can be attributed to the sound card, the speaker, consumer headphones, cabling, connectors, etc. In addition to the aforementioned obstacles related to audio characteristics, the calibration of acoustic signals emanating from a consumer transducer (a consumer earphone, for example) represents a daunting challenge, preventing accurate hearing evaluation by the lay consumer using a personal computer, or a personal electronic device.

Hearing screening tests offer basic hearing assessment for individuals on the basis of a pass or fail criteria. Generally speaking, these tests are administered by a hearing professional or a nurse, using a portable instrument, which produces a limited set of test stimuli often at a predetermined level between 20 and 40 dB HL depending on the age of the group being tested. These tests generally vary according to the guidelines of the agency, state, and country. Similar to standard audiometric evaluations, tonal and narrow-band noises are generally presented to administer the hearing screening test. One major drawback of current hearing screening methods is the lack of sensitivity and specificity for determining the hearing ability and indicating hearing aid candidacy. As a result, "failed" subjects are generally referred to a hearing professional for further hearing assessment prior to hearing aid candidacy assessment and hearing aid fitting.

SUMMARY

The present disclosure describes example systems and methods for calibrated evaluation of a consumer's hearing ability and hearing aid candidacy, without requiring clinical instrumentation and professional settings. In some embodiments, the hearing evaluation uses standard personal computers in conjunction with an audio signal generator device configured to generate calibrated audio signals to administer a rapid hearing profile test in the consumer's environment, such as the consumer's home or office. In some embodiments, the audio signal generator device may be handheld and worn on the body or placed on a table during the hearing test. The hearing profile test presents a sequence of supra-threshold test stimuli, generally above 20 dB HL with increments in the range of 10-20 decibels, up to test levels of approximately 70-80 dB HL. The test signals may be presented in frequency bands in the range of 400-8000 Hz. The consumer's minimum audibility response within the suprathreshold sound level range presented at each test frequency band may be registered using a personal computer, which may comprise a smartphone or a tablet computer. The personal computer executes a hearing profile software application to implement the hearing profiling method described herein, and to present a computed hearing profile score, indicting the general hearing ability and hearing aid indication. The hearing profile score may be whole or fractional, for example indicating approximately one of five discrete levels or categories of hearing ability. The entire evaluation process, including profiling, scoring and hearing aid indication, may take approximately less than 10 minutes, in one embodiment. The cost to a consumer may be less than $50, including minimal incremental hardware and software to administer the calibrated test using a personal computer virtually anywhere, including at home.

In an example embodiment, the acoustic stimuli presented are in the suprathreshold range of 30-80 dB HL, with a test increment of approximately 10 decibels, presented at frequency bands of 500, 1000, 2000, 4000 and 6000 Hz. The score may be computed based on minimal audibility level (MAL) within the suprathreshold range presented, and weighted by appropriate factors such as the speech intelligibility index (SII) as per American National Standards ANSI/ASA S3.5.

In one example embodiment, the delivery of the acoustic test signal from the hearing profile evaluation system may be provided by a standard consumer-type earphone with calibrated electroacoustic performance. The earphone may be provided with insert eartips, to occlude the ear canal and reduce the audibility of ambient background sounds present in typical room environments. By limiting the test presentations to suprathreshold levels, generally exceeding 20 dB HL, and using ear occluding eartips, hearing profiling may be performed in any reasonably quiet room environments, eliminating the cost and inconvenience of specialized earphones and clinical settings. In one embodiment, a microphone may be incorporated to sense the level of ambient background noise and adjust the hearing evaluation process accordingly. By reducing the range of presentation levels and test frequencies, increasing the test increment level to 10 dB or more, and providing a simplified scoring system, the lay consumer may be presented with an alternative hearing evaluation method that is easy to understand and correlate to hearing device candidacy.

In one embodiment, one or more natural sounds are presented as calibrated test signals. For example, a drum sound may be presented for testing the low frequency range of hearing, and a bird chirp sound may be presented for testing the high frequency range of hearing. The hearing profile test may be administered online with a hearing profile software application at least partially hosted by a remote server and executed by the consumer's own personal computer that is connected online to the remote server and to the handheld audio generator device at the consumer side. The online computerized hearing test system may be advantageous by offering online support during the hearing evaluation process. In one embodiment, a customer support personnel may send speech communications online from a customer support computer system into the test earphone. The customer support personnel may also use the customer support computer system to receive speech communications online from the consumer by the aforementioned microphone using Voice-Over Internet Protocol (VoIP) communications.

BRIEF DESCRIPTION OF THE DRAWINGS

The above objectives, features, aspects and attendant advantages of the present invention will become apparent from the following detailed description of various embodiments, including the best mode presently contemplated of practicing the invention, when taken in conjunction with the accompanying drawings, in which.

DETAILED DESCRIPTION

Certain details are set forth below to provide a sufficient understanding of embodiments of the invention. Some embodiments, however, may not include all details described herein. In some instances, some well-known structures may not be shown, in order to avoid unnecessarily obscuring the described embodiments of the invention.

Figure 1:
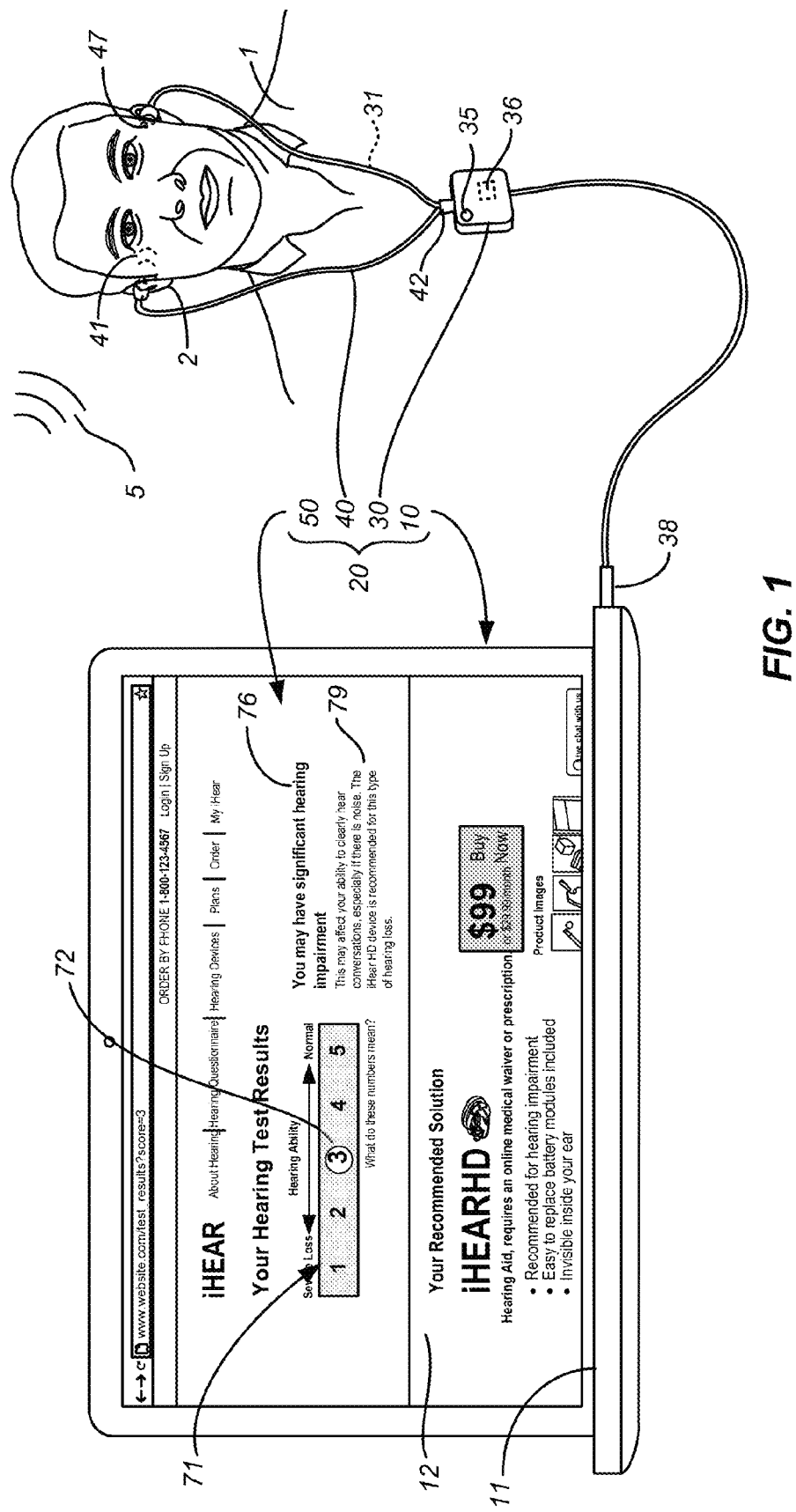
FIG. 1 is a view of a computerized hearing test system, including a handheld device comprising an audio signal generator for generating calibrated audio signal, a personal computer and an insert earphone for producing calibrated test sounds, according to one embodiment.

The present disclosure describes example systems and methods, as shown in FIGS. 1-13, for profiling the hearing ability of a consumer and indicating hearing aid candidacy rapidly and inexpensively without requiring expensive equipment and clinical settings. Referring to FIG. 1, in one embodiment, the evaluation process uses a general purpose computing device, for example a standard personal computer 10, in conjunction with a handheld device 30 configured to generate a calibrated audio signal 31 (also referred to herein as "test audio signal" and "audio signal") to earphones 40 to administer a hearing test in the consumer's normal environment, such as the consumer's home or office. The personal computer 10, the handheld device 30, hearing profile software application 50, and the earphones 40 may collectively form a computerized test system 20 (also referred to herein as "computerized hearing test system"). The computerized test system 20 presents a sequence of supra-threshold test stimuli 41, generally above 20 dB HL, into the ear 2 of the consumer 1. For reference purposes, 0 HL represents the threshold of hearing for normal hearing individuals, and suprathreshold refers to sound levels above the threshold of normal hearing. Also, 20 dB represents a significant increase over threshold levels, from the sound level perspective, as well as electrical signal requirements for the electrical audio signal 31 producing the acoustic test stimuli 41. In various embodiments, the test stimuli 41 may be provided in step levels in the range of 10-20 dB, in contrast to standard audiometric test methods which specify 5 dB increments, for example as per ANSI/ASA 3.6 standard.

Figure 2:
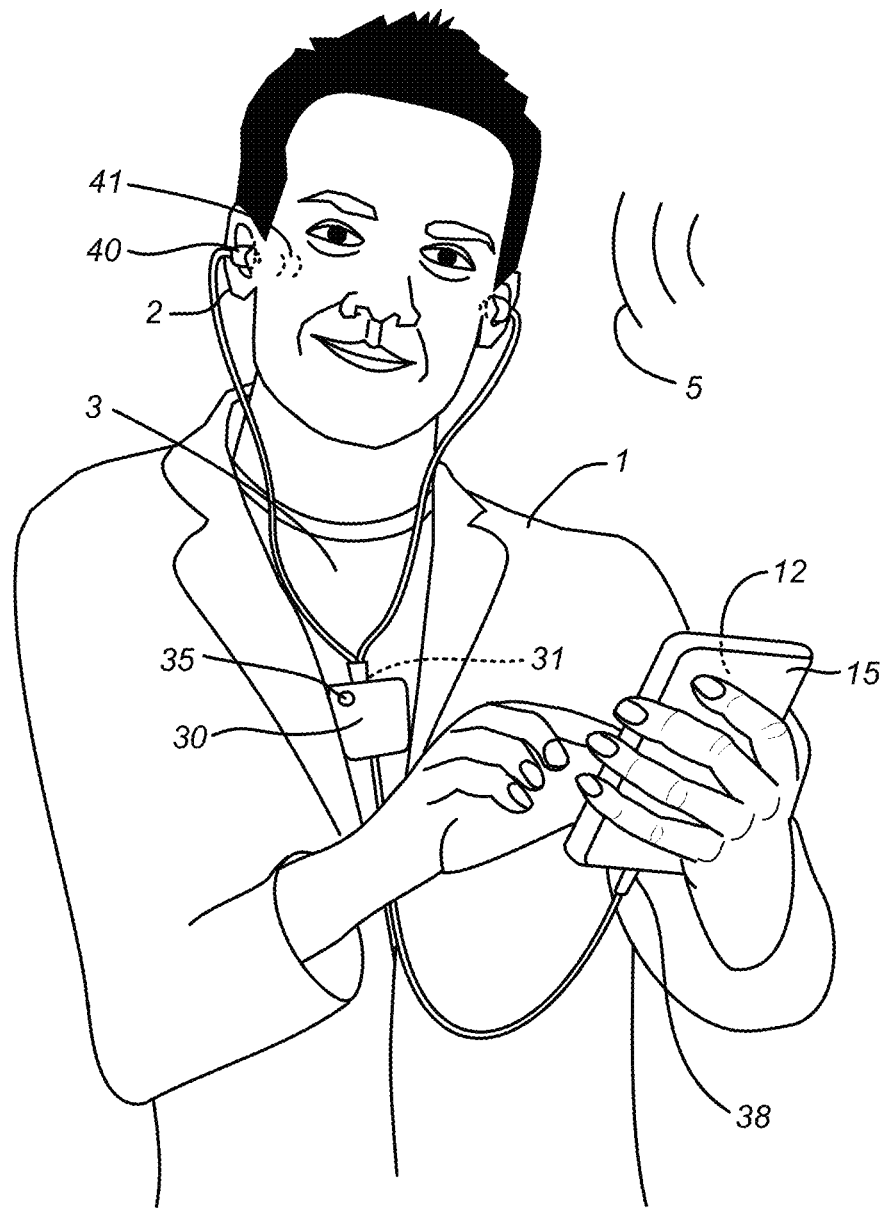
FIG. 2 is a representation of a hearing profile test system using a smart phone and a handheld device clipped on the shirt of a user, according to one embodiment.
Figure 3:
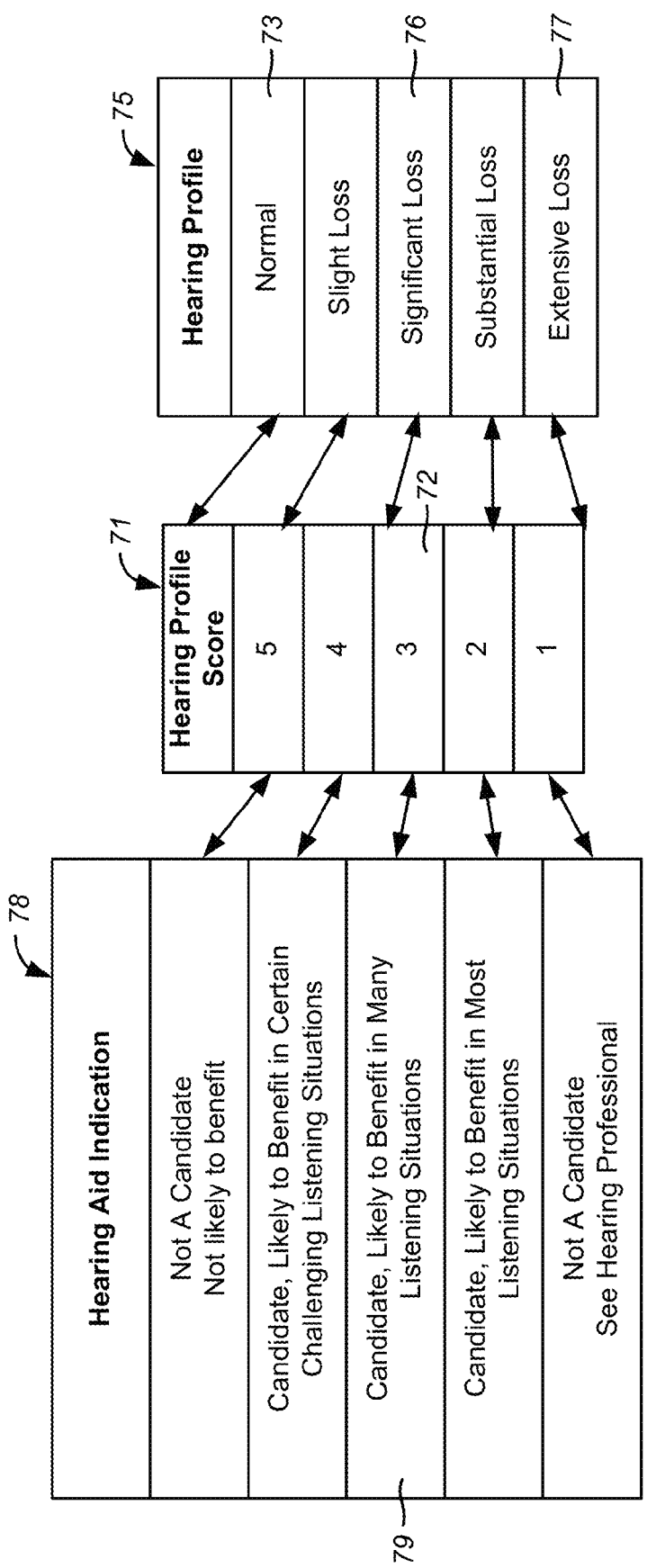
FIG. 3 is a representation of a hearing profile scoring system, including hearing profile categories, hearing profile score scale, and indication of hearing aid candidacy indication, according to one embodiment.

FIG. 2 shows a smartphone embodiment of a computerized hearing test system with a handheld device 30 connected to smartphone 15, executing a hearing evaluation application for self-administration. The user 1 follows instructions and registers audibility responses using the touch screen 12 of the smartphone 15. Similarly, a hearing profile score 72, hearing profile 76 (also referred to herein as "hearing ability"), and hearing aid candidacy 79 are presented to the user following the hearing profile test. The computerized hearing test system 20 may be implemented to enable rapid and sufficiently accurate assessment of a consumer's hearing ability in environments outside clinical setting, and to provide easy to understand scoring system with hearing ability scale 75 and hearing aid candidacy scale 78.

In one embodiment, the acoustic test stimuli 41 may be presented at three or more frequency bands within the audiometric frequency range of about 400 to 8000 Hz. The consumer's minimum audibility level (MAL) within the suprathreshold (with respect to normal hearing) range of sound levels presented at each test frequency band may be registered using the personal computer's standard interface, such as a keyboard 11, mouse, or touch screen 12. The personal computer 10 may also be in the form of a smartphone 15 as shown in FIG. 2, or a tablet computer (not shown). A personal computer herein generally refers to any consumer computing device capable of executing a hearing profile software application 50 according to the teachings herein. After executing the hearing profile test (also referred to herein as "hearing test" and "hearing profile evaluation"), the consumer 1 may be presented with a hearing profile score 72 (FIG. 3) from a hearing profile score scale 71, with each hearing profile score (HPS) corresponding to a hearing profile within hearing profile scale 75, and hearing aid candidacy indication within hearing aid indication scale 78. The levels within the hearing profiling system may be in the range of about 4-6 discrete levels or categories. Throughout this application, the term "consumer" refers to any person taking the hearing test and is interchangeable with other, similar terms, including but not limited to "user," "person," "client," "hearing impaired," "tester," "test subject," etc. The term "hearing aid," is used herein to refer to all types of hearing enhancement devices, including medical devices generally prescribed for the hearing impaired, and personal sound amplification products (PSAP) generally not requiring a prescription or a medical waiver.

In some example embodiments, the suprathreshold level of acoustic test stimuli 41 may be limited to a range of about 30-80 dB HL, with level increments in a range of about 10-20 dB between consecutive stimuli, at multiple frequency bands within a range of about 500-6000 Hz. The hearing profile score, 72 for example, is generally based on a computation incorporating the minimal audibility levels at the test frequencies. The scoring computation may optionally incorporate, at least partially, frequency weighting factors, such as the speech intelligibility index (SII) as per ANSI S3.5 standard, as will be described in more details in an example below. In one aspect, the consumer 1 is offered a simplified scoring system for indicating hearing ability and hearing aid requirements.

In some embodiments, the acoustic test signal 41 from the computerized hearing test system 20 may be delivered via an earphone 40 with an eartip 47 (FIG. 4), also referred to here as ear canal "insert," which occludes the ear canal and minimizes the adverse effects of ambient background noise 5 (FIG. 1) present in room environments during the hearing profiling process evaluation. The insert 47 is connected to the earphone earpiece 46 incorporating a transducer (not shown) within. In the preferred embodiments, the eartip 47 provides at least 5 dB of noise attenuation, within the audiometric range of 500 Hz to 6,000 Hz. Noise herein generally refers to sounds which may compete with the test stimuli 41 presented to the ear 2 by the earphone 40, which may be insert type (as shown) or circumaural headphone (not shown). The insert 47 may be removable and offered in assorted sizes, for example with a relatively large eartip 48 as an alternative for individuals with relatively larger ear canals. In some embodiments, an assortment of 3-4 eartips may be provided, to ensure proper fit in variety of ear canal sizes. By presenting calibrated acoustic test signals 41 at suprathreshold levels generally exceeding 20 dB HL, and in combination with an occluding earphone 40, a hearing profile evaluation may be administered in a typical room environment, as is further described below.

To further mitigate the effects of potentially excessive noise in certain room environments, a microphone 35 (FIG. 1) may be incorporated within the handheld device 30 to sense room sound 5 in the vicinity of the user 1. The hearing profile test process may then be adjusted according to the noise condition, for example by delaying the presentation of test stimuli 41 during a noise burst, or by halting the test process in the presence of persistent or excessive noise.

Figure 10:
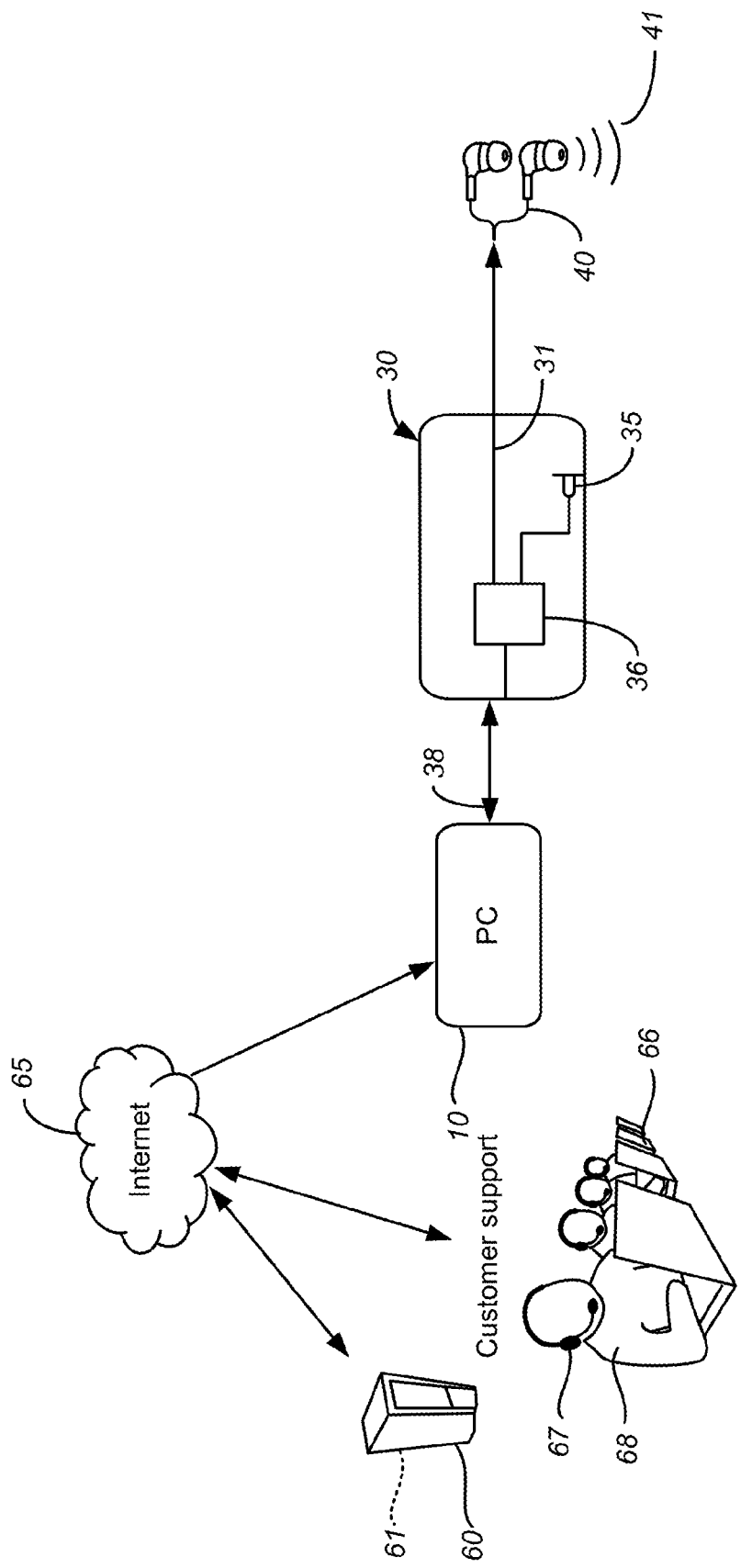
FIG. 10 is a diagram depicting an example online hearing profile test system, including a remote server for hosting a hearing profile test application and a remote customer support computer system and personnel, according to one embodiment.

In some embodiments, the handheld device 30 is placed generally on the user's body in proximity to the ear 2, for example on the torso 3 area as shown in FIGS. 1 and 2. In some embodiments, the handheld device 30 may be affixed to the user's shirt or jacket with a clip (not shown) or held by a necklace (not shown). The computerized hearing test system 20 and methods thereof allow rapid and accurate hearing profiling for a lay person with minimal hardware by leveraging their own personal computing device while presenting calibrated test audio signals 31 by the handheld device 30. In some embodiments, the computerized hearing test system 20 is designed primarily for self-administration. However, it should be understood that assistance may be provided for certain individuals, for example those with limitations related to aging, heath condition, or mental capacity. The handheld device 30, in some embodiments, includes a USB interface 38 for interfacing with, and control by, a personal computer 10, and in some cases for streaming of digital audio representing test signals or audio instructions from the personal computer 10. Digital audio files representing test stimuli, as well as calibration constants associated with calibrated test stimuli, may be stored within the handheld device 30, within the client personal computer 10, on a remote server 60 (FIG. 10), or generally anywhere on the Internet "cloud" 65 (FIG. 10). The handheld device 30 houses audio signal generator 36 (also referred to herein as "digital audio system"), and includes programmable audio amplifiers to provide calibrated test audio signals 31. The digital audio system is generally independent of the personal computer 10 audio capabilities, and may be configured to provide calibrated audio signals 31 regardless of the computer platform used by the consumer 1. This allows for predictable audio characteristics conforming to accepted standards, for example as per ANSI/ASA 3.6. In preferred embodiments, a single-chip digital audio system is employed within the handheld device 20 to convert digital audio data from the personal computer 10 to a predetermined level of audio signal 31 for delivery to the earphone 40, generating a calibrated test stimuli 41 signal to the ear 2. The term "calibrated" herein generally refers to the terms "known," "determined," "predetermined," and similar terms to describe an electrical or an acoustic signal having predicted characteristics, whether by a design or by a calibration process, to conform to a standard or a design specification.

Figure 4:
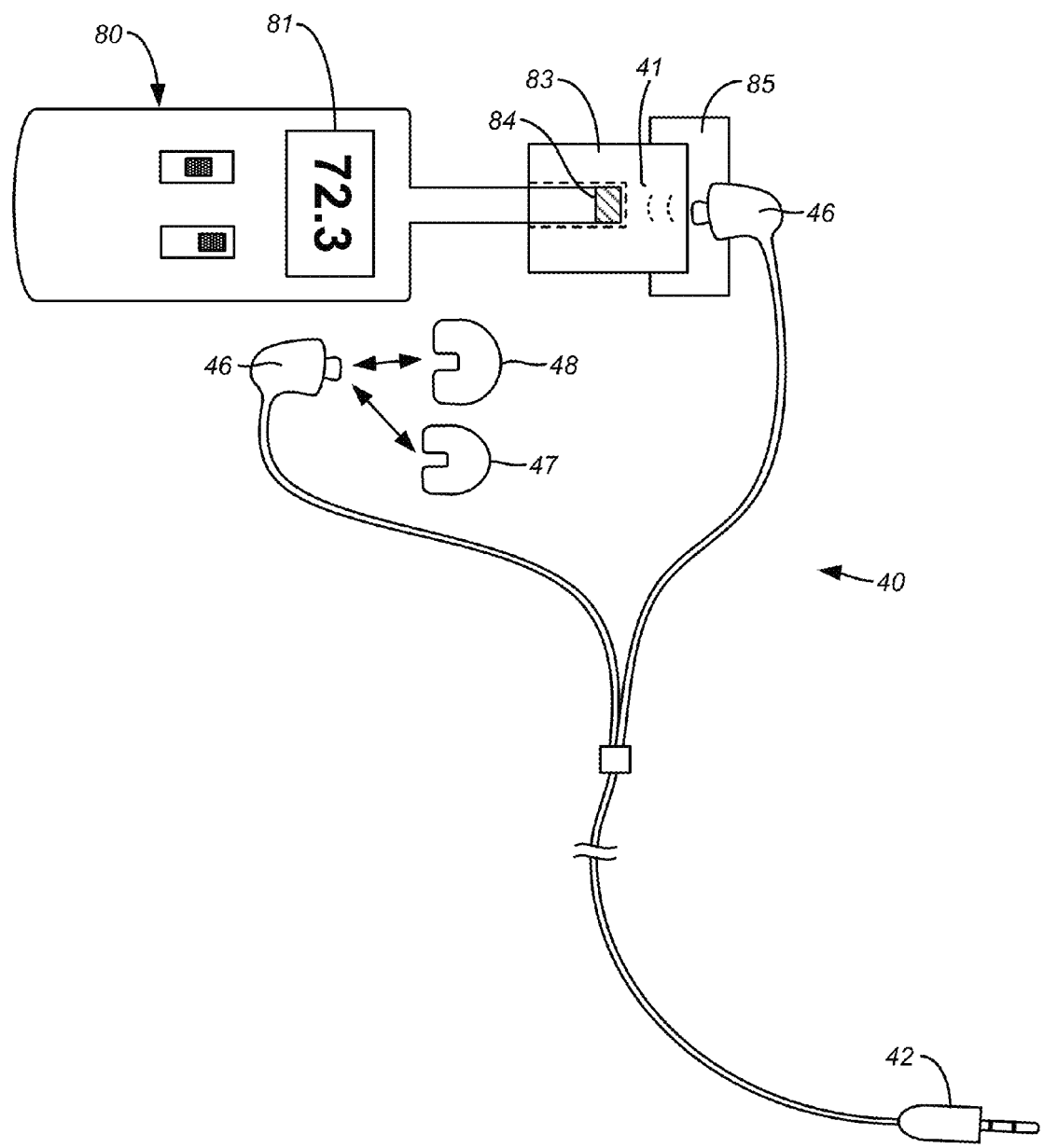
FIG. 4 is a view of a calibration system for standard consumer type earphones, with assorted eartips, a 2-CC acoustic coupler, earphone-coupler interface, and a sound level meter, according to one embodiment.

FIG. 4 shows one embodiment of a system for calibrating a standard earphone 40 using a standard 2-cc coupler 83 and a sound level meter 80. The eartip 47 or 48 may be removed from the earphone earpiece 46 and coupled to the 2-cc coupler, using an earphone-coupler interface 85. A microphone section 84 of the sound level meter 80 is typically inserted into the 2-cc coupler cavity for calibrating the sensitivity of the earphone earpiece 46, using the sound level measured and presented at the display 81 of the sound level meter 80. The calibration of the earphone 40 is preferably performed by the manufacturer or calibration service provider for the handheld device 30, and generally not of concern for the consumer 1. The consumer 1 may plug the audio connector 42 of the earphone 40 into the handheld device 30 and plug USB connector 38 of the handheld device 30 into the personal computer 10. The consumer 1 may then begin the testing, using the hearing profile software application 50 (FIG. 11) provided to the consumer 1 for execution by the personal computer 10, and by the handheld device 30, which may be configured to deliver calibrated test signals 31.

In one embodiment, one or more natural sounds may be employed as test stimuli 41 to engage the consumer with sounds relevant to the human hearing experience. In contrast to traditional methods, which employ tonal sounds, natural sounds represent sounds audible in normal listening experiences, such as human speech, music, animal sounds, bird chirp, wheel squeak, etc.

Figure 5:
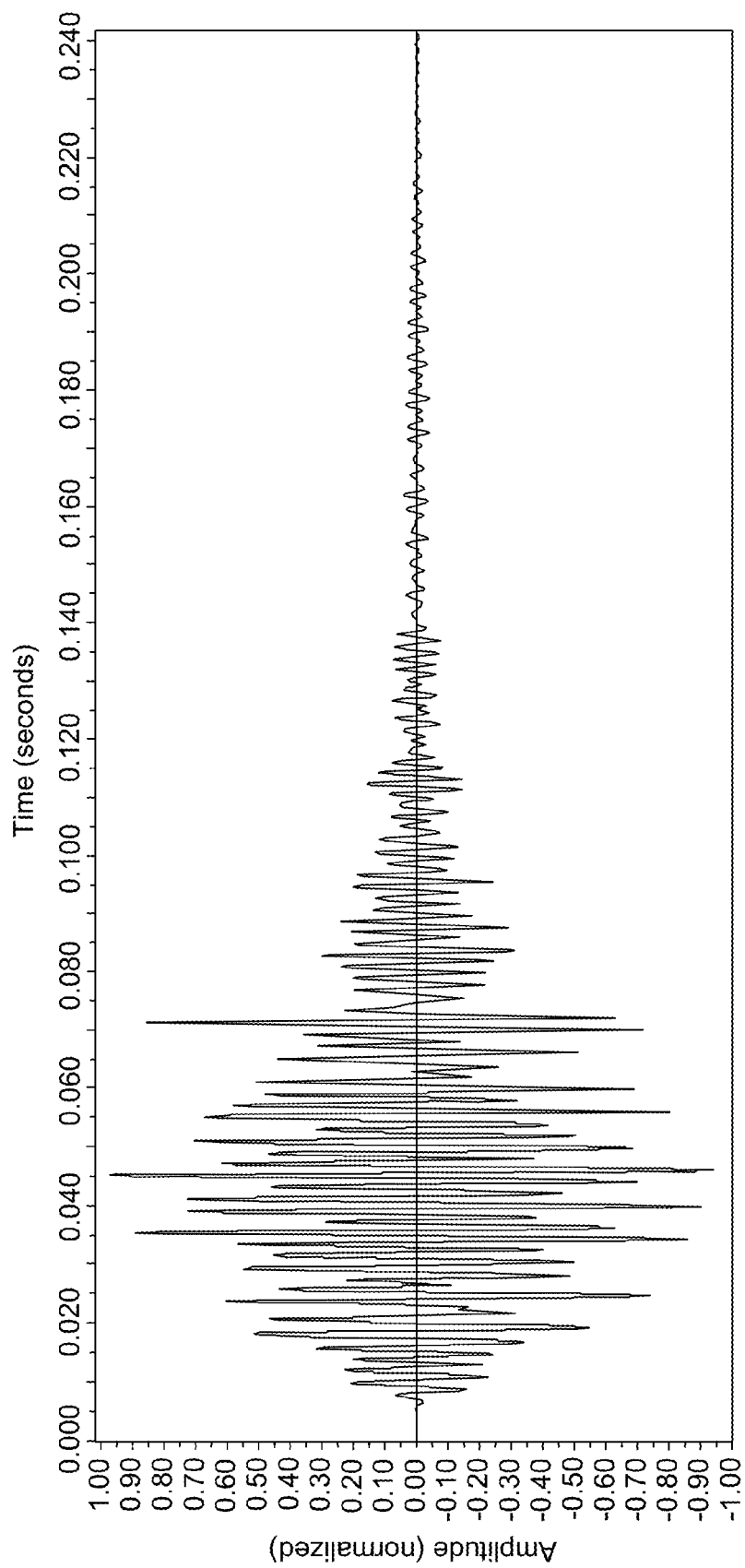
FIG. 5 is a time domain graph of a test signal from a drum snare sound recoding for evaluating the hearing ability in the low frequency at a 500 Hz band.
Figure 6:
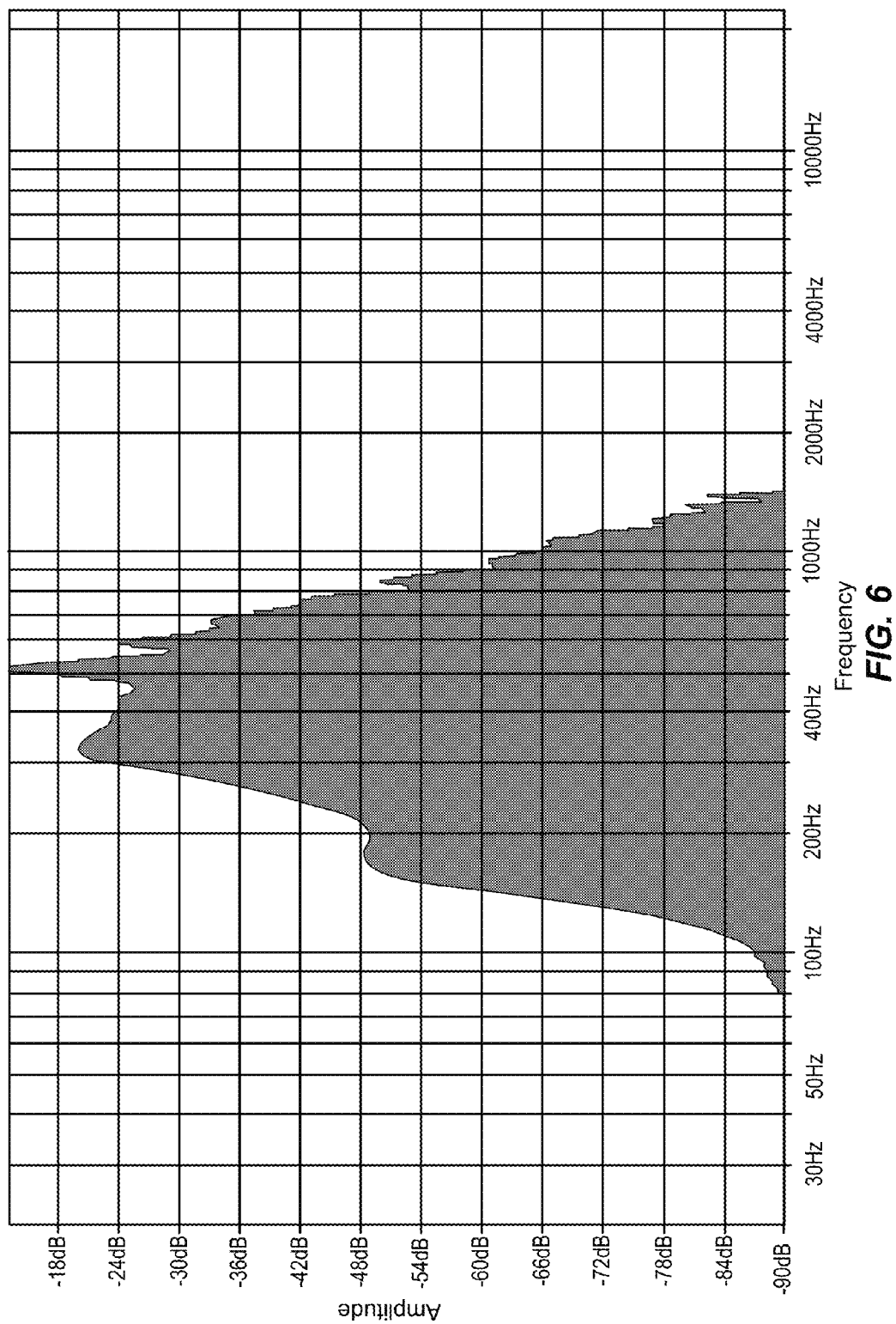
FIG. 6 is a frequency spectrum graph of the drum snare test signal of FIG. 5.

In an example embodiment, a drum snare sound recording may be used to test the hearing ability of the consumer 1 at a relatively low frequency range of audible sound, as shown in FIGS. 5 (waveform) and 6 (frequency spectrum). A drum snare sound generally has significant content in the low frequency portion of the human auditory range, for example around 500 Hz. With further processing by an audio processing software, for example AUDACITY® for Windows, the original drum snare recording waveform may be modified to result in a frequency response peaking at approximately 500 Hz and with reduced frequency content outside the 500 Hz frequency band as shown in FIG. 6. Alternatively, a hammer sound may demonstrate similar spectral characteristics and may be employed for hearing testing in a low frequency range.

Figure 7:
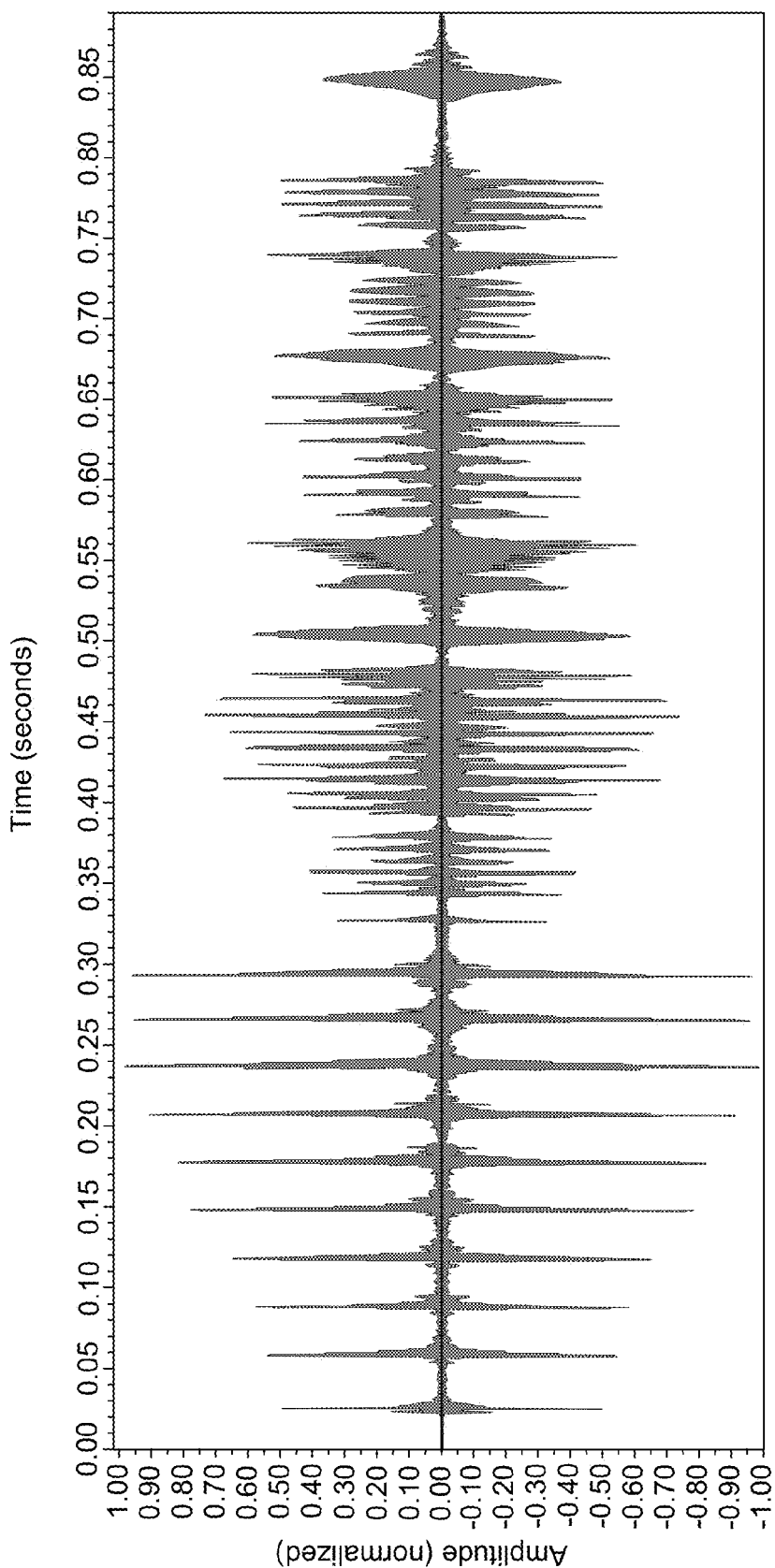
FIG. 7 is a time domain graph of a test signal from a bird chirp sound recording for evaluating the hearing ability in the high frequency at a 6000 Hz band.
Figure 8:
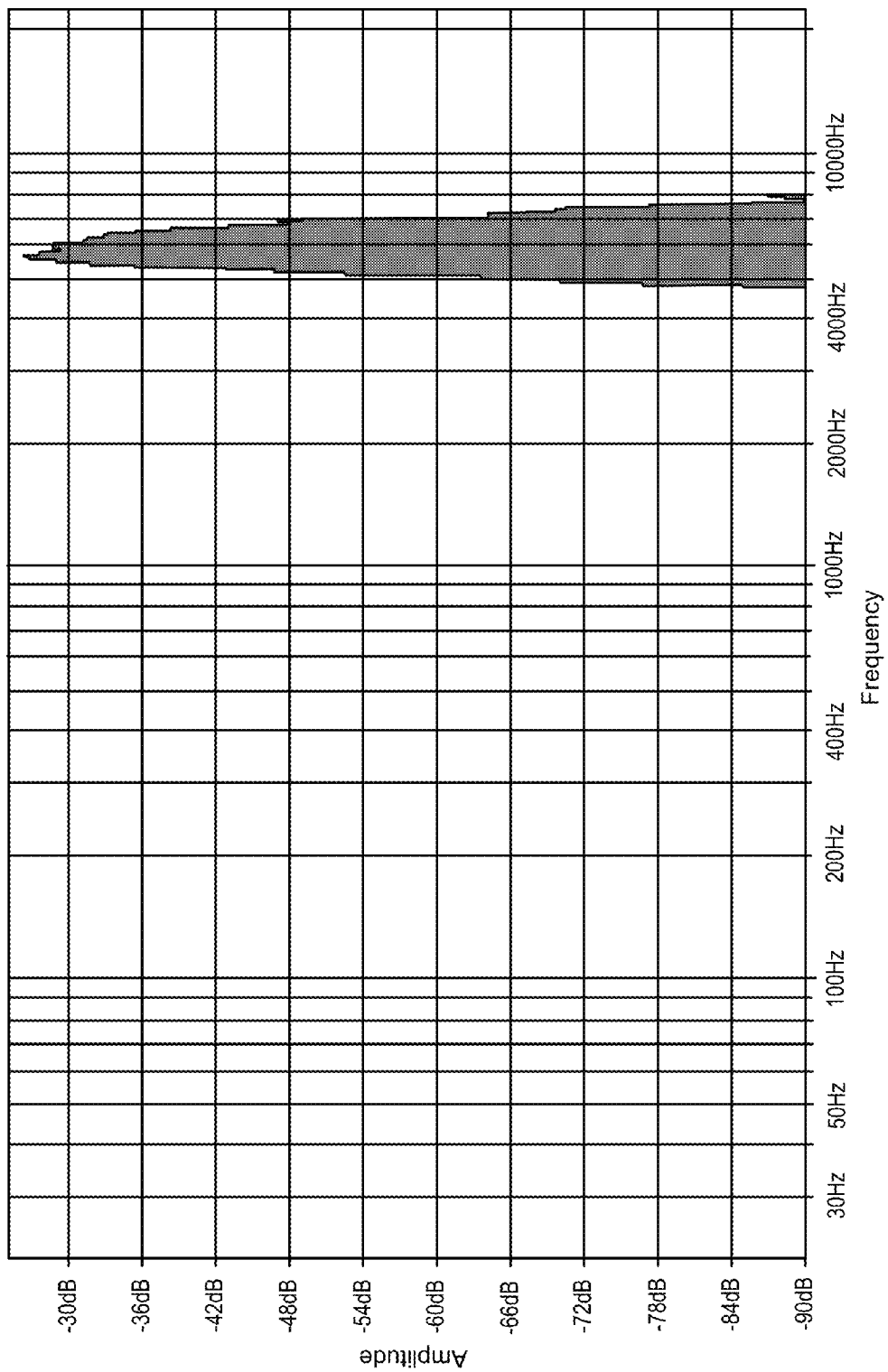
FIG. 8 is a frequency spectrum graph of the bird chirp test signal of FIG. 7.

In another example, a bird chirp sound recording may be employed for testing hearing of the consumer 1 at a relatively high frequency range, as shown in FIGS. 7 (waveform) and 8 (frequency spectrum). A bird chirp sound generally has significant content in the high frequency portion of the human auditory range, for example around 6000 Hz. The original bird chirp recording may also be filtered by an audio processing software to produce a test signal substantially in the high frequency range, for example around 6000 Hz frequency band, as shown in FIG. 8.

Figure 9:
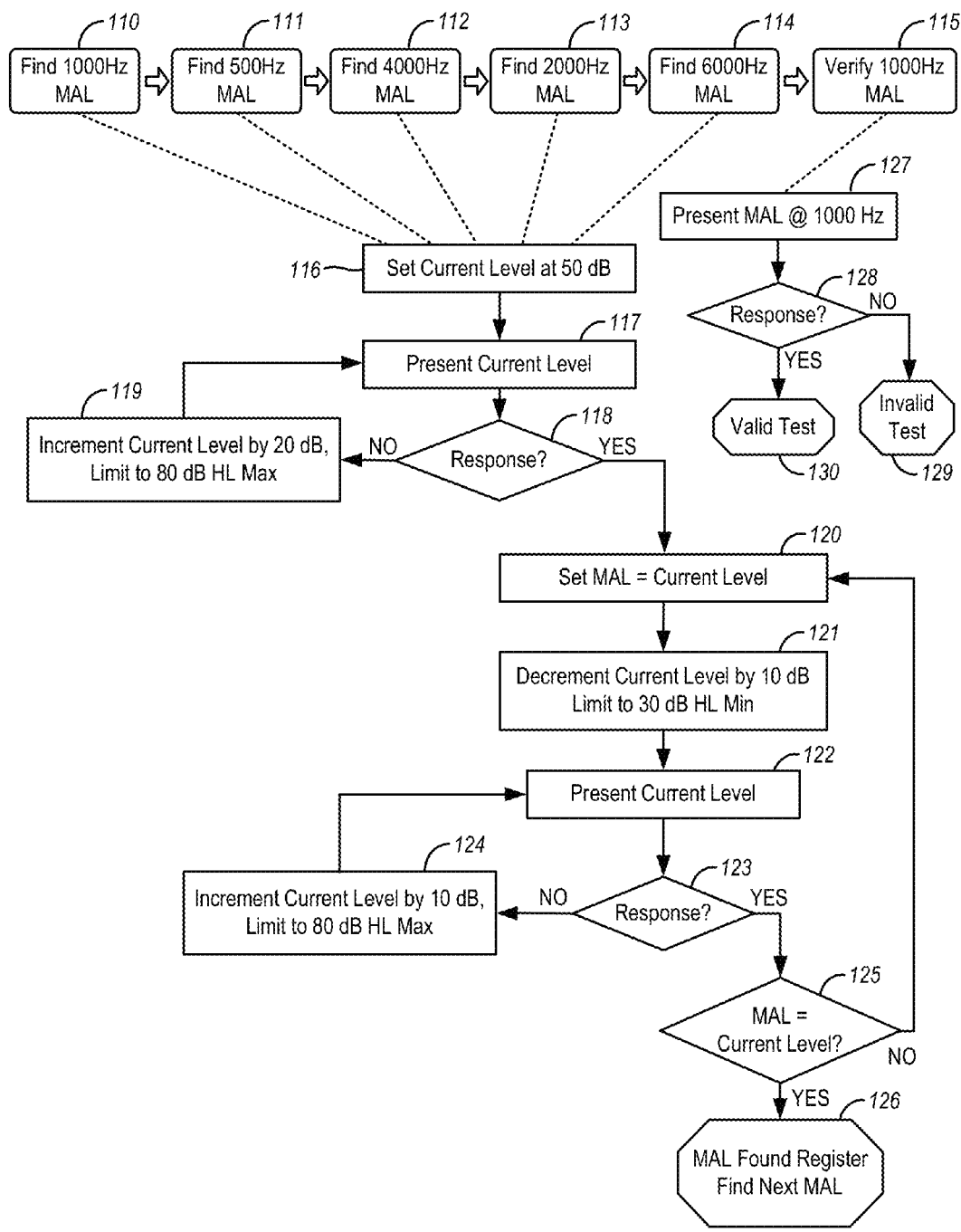
FIG. 9 is a flow chart depicting a simplified example process for automatically presenting test signals and determining minimum audibility levels, according to one embodiment.

FIG. 9 shows a simplified example flowchart for an automatic hearing evaluation process for determining the minimum audibility level (MAL) of the consumer 1 within the range of the suprathreshold sound levels presented. As shown in the flowchart with operations 110-130, starting with determining MAL at 1000 Hz. (operation 110), a signal level of 50 dB HL may be initially set (operation 116) and test stimuli 41 is presented at 50 dB HL (operation 117) to the consumer 1. The response from the consumer 1 is then determined by operation 118 and if no response is registered by the computerized hearing test system 20 within a time window, typically 1 to 1.5 seconds from the end of the stimuli period, the "current level" of the test stimuli 41 is incremented by 20 dB HL, up to a maximum level of 80 dB HL for example (operation 119) and the test stimuli 41 is then presented to consumer 1 at the increased level (operation 117). When a response is detected in operation 118, an MAL value is recorded (operation 120) for subsequent verification by operations 120-126 whereby the test signal level is decremented by 10 dB (operation 121) and presented (operation 122) for response determination (operation 123). If a response is not registered at operation 123, the test stimuli level is incremented by 10 dB (operation 124) and the test stimuli is presented (operation 122) with the increased level, and the process is repeated if necessary, until a response is registered at operation 123. The MAL for a test frequency is considered "found" (operation 126) generally when the computerized hearing test system 20 detects two consumer responses at the same presentation level as determined by operation 125, which compares a currently registered response level with a previously recorded MAL. If the current response level does not match the previously recorded MAL, a new MAL value is set and recorded (operation 120) and the signal level is decremented by 10 dB (operation 121) until an MAL is determined (operation 125). In the preferred embodiments, the step size for consecutive test presentations is within the range of 10-20 dB.

The process for determining MALs for all test frequencies (operations 110-114) may be sequenced as in shown in FIG. 9, or interleaved (not shown), either randomly or at a predetermined interleave sequence. Interleaving may minimize predictability of test process sequence by the consumer 1 and may improve the reliability of the test. A final verification process (operation 115) at one frequency, typically at 1000 Hz, is preferably administered to assess the reliability of the user's responses. For example by re-presenting a 1000 Hz test stimuli 41 (operation 127) at the MAL previously determined in operation 110, and determining if the consumer 1 is responding consistently at this level (operation 128), and to determine either a reliable "valid test" (operation 130) or inconsistent "invalid test" (operation 129). It should be understood that variations of the aforementioned example hearing evaluation process and algorithm thereof are possible and may be advantageous.

Known attempts to address the issues and limitations of current audiometry methods include providing embodiments of automatic hearing testing and hearing aid programming integrated in a unitary headset instrument. These embodiments offer conventional test stimuli to compute standard prescriptive formulae to program into a hearing aid. Known attempts also include online home testing using the consumer's own personal computers and the consumer's own headphones or the computer's speakers. To circumvent issues related to signal quality and calibration, online tests generally employ signal-in-noise conditions, mainly to detect the person's ability to hear in the presence of noise. Although they may be valuable in assessing the hearing ability for certain types of losses, these signal-in-noise tests fail to indicate the level of hearing loss, and are considered as screening tools requiring further assessment by a hearing professional using diagnostic hearing assessment tools.

In an online embodiment of the hearing evaluation method of the present invention shown in FIG. 10, a hearing test software application 61 is hosted by a remote server 60 and executed locally by the consumer's personal computer 10, as a client computer connected online to the server 60 via the Internet 65. The hearing test software application 50 executed by the computer 10 is at least partially hosted by the server 60, in the example online embodiment. The results of the hearing evaluation, including the hearing profile store, may be stored in a remote database.

The online computerized hearing test system may further offer online customer support by connecting to a customer support computer system 66 operated by customer support personnel 68. The customer support personnel 68 may communicate with the consumer 1 by a headset 67, including a microphone to stream instructions from customer support computer 66 to the consumer 1. For example, voice over IP (VoIP) may be used to stream instructional audio to the client computer 10, to the digital audio system 36 of the handheld device 30 via the USB connectivity 38, and ultimately as audible stimuli 41 to the consumer's ear 2 via the earphone 40. Instructional audio may include the speech of customer support personnel 68, recorded or generated audio massages from a server 60 or customer support computer 66. Speech communication from the consumer 1 may also be transmitted to the customer support personnel 68 by the reverse process, using the microphone 35 of the handheld device 30, or another microphone incorporated in the computerized hearing test system 20.

Figure 11:
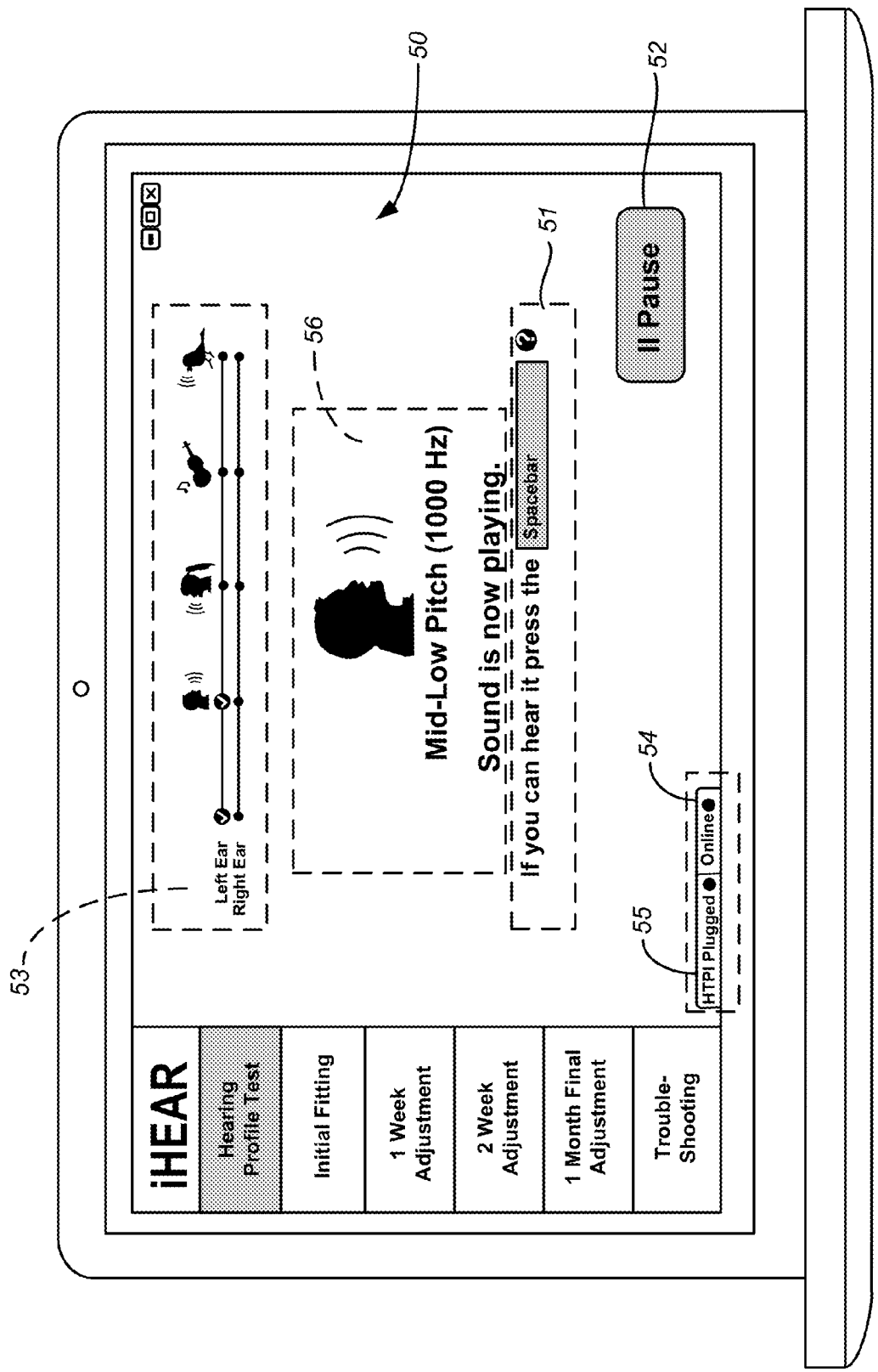
FIG. 11 is a view of a hearing profile test user interface from a web browser, with test in progress, according to one embodiment.

FIG. 11 shows an example user interface (UI) 50 for an online embodiment of the hearing evaluation method, employing a web browser to execute a server hosted hearing profile software application. The UI 50 shows UI elements, including user instructions 51, test pause control 52, test presentation status 56, test process status 53, online connection status 54, and handheld device 20 connection status 55. In this embodiment of the user interface 50, the user 1 is generally instructed to listen to the calibrated test sounds 41 presented and press the space bar of the keyboard 11 (or a key on the touch screen 12) when the sound 41 is heard. In one embodiment, the browser-based application operates in conjunction with a client application, which provides access to, and control of, the handheld device 30.

Figure 12:
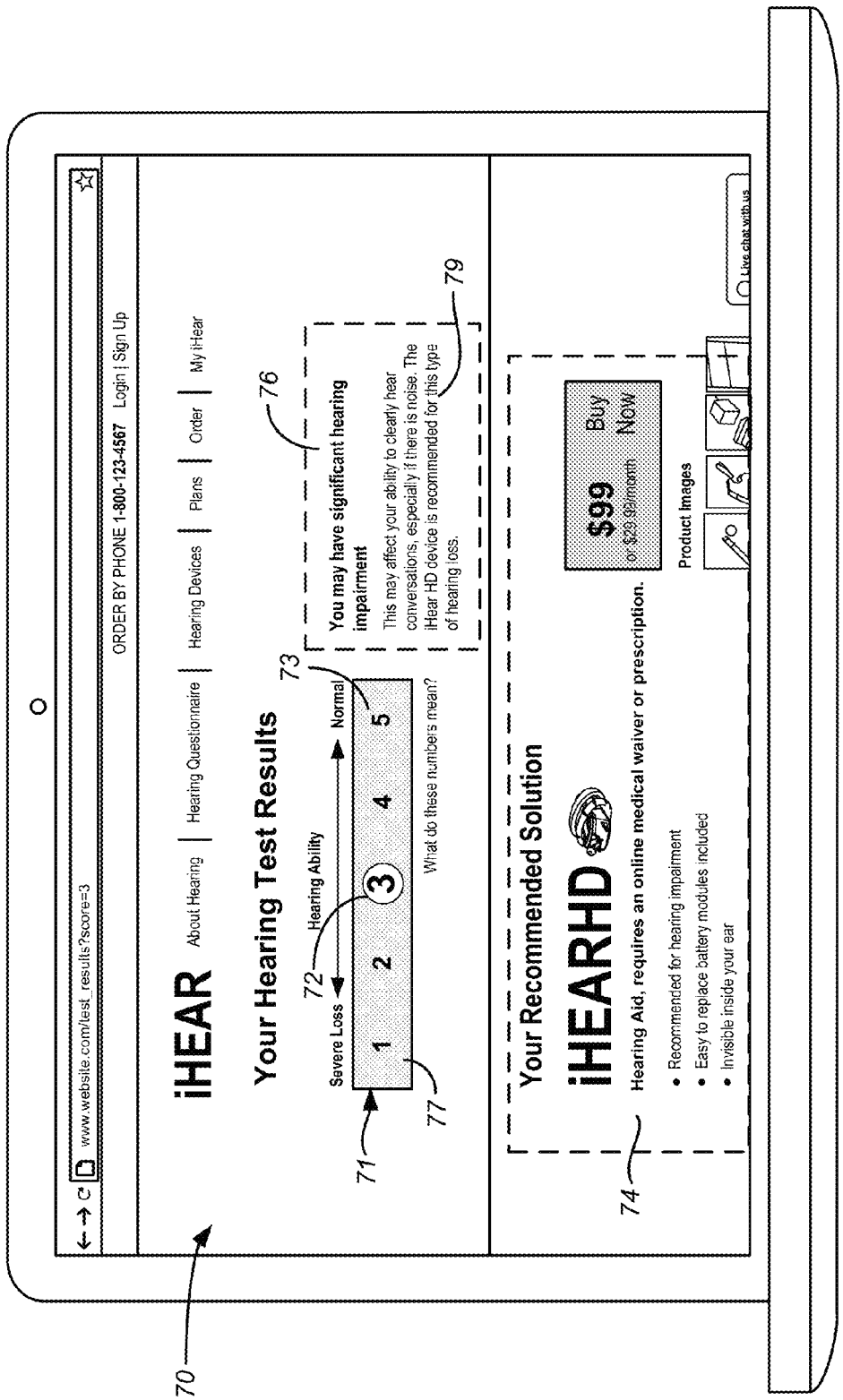
FIG. 12 is a front view of a hearing profile test scale and score presented on a browser user interface, indicating hearing aid candidacy and a hearing aid recommendation, according to one embodiment.

FIG. 12 shows an example representation of the hearing profile scoring UI 70, showing hearing profile score 72, hearing profile score scale 71, and hearing ability 76 and hearing aid indication 79. Contrasting the hearing profiling system disclosed herein with standard audiogram reports, which display the sensitivity of hearing from −10 to 110 dB and in a reverse order without indicating hearing ability or candidacy, the hearing profile score 72 and corresponding hearing ability 76 and hearing aid candidacy 79, indicates the general ability to hear from "Normal" 73 to "Extensive" 77, suggesting professional assessment and/or intervention. Hearing aid candidacy 79 may be computed at least partially from the hearing profile score, and in some cases other factors may also contribute.

Figure 13:
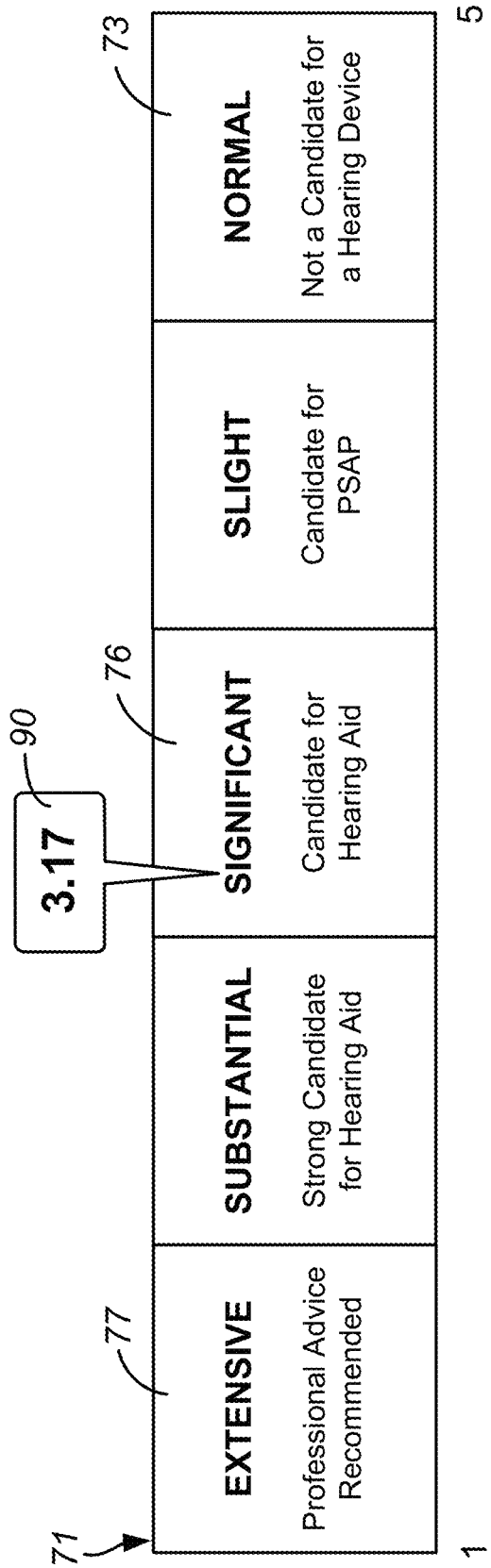
FIG. 13 is a representation of a fractional hearing profile test score presented in conjunction with a scale descriptive of hearing ability and hearing device candidacy, according to one embodiment.

FIG. 13 shows an alternate embodiment of the hearing profile scoring scale 71, whereby the scale is primarily descriptive, and a fractional hearing profile score 90 is presented in conjunction with the descriptive scale. In some examples, the fractional hearing profile score 90 may be presented as an overlay, that is on top of the scoring scale 71, in order to provide the consumer 1 with a more precise score while also pointing to general descriptive context. According to various alternative embodiments, suitable variations of the scoring system and method and corresponding indications may be made, such as reversing the order of the scoring scale 71, with level 1 representing "Normal Hearing" and the highest level representing worst hearing ability. Alternatively, alphanumeric character representation, such A, B, C, etc., may be used to represent the hearing ability. In the preferred embodiments, the scoring levels may be limited to 4-6 categories. The web page UI 70 of FIG. 12 also shows a hearing aid recommendation section 74, describing product and pricing options to the consumer.

In contrast to conventional audiometric test methods and reports, the systems and methods disclosed herein simplify and expedite the test process by eliminating various redundancies and limiting the hearing evaluation to test signals relevant to hearing aid candidacy and fitting, generally at levels above 20 dB HL and frequencies above 500 Hz and up to 6,000 Hz. This is particularly applicable when considering the fitting systems and methods that use subjective assessment by the consumer for determining hearing aid fitting parameters during the fitting process. By eliminating testing below 500 Hz, the adverse effects of low frequency noise commonly present in room environments may be substantially mitigated.

Experiment

The following experiment was conducted to assess and validate the hearing profile test in normal room environments according to the teachings disclosed herein. Sound measurements were taken in an office with two personal computers operating and the test instruments used to conduct the experiment. Fan noise from the computers and street noise were noticeably audible by non-occluded ears. The measurements were taken approximately 4 feet away from the nearest computer. The room noise level was measured using a 2-channel spectrum analyzer (Stanford Research model SR 785), two probe tube measurement systems (ER-7 manufactured by Etymotic Research) and an integrating sound level meter (Model 2200 manufactured by Quest). This experiment is reported here by way of example and to facilitate understanding and appreciation of the system and methods described herein. Inclusion of this experiment here is in no way intended to represent that all experiments performed did or will achieve like results.

Room noise was initially measured by the sound level meter, indicating average noise level of about 44 dB SPL. Using the spectrum analyzer and the probe tube system, the average noise level in ⅓ octave bands was measured for frequencies between 500 and 6000 Hz frequencies as tabulated in Row-A of Table 1. The attenuation across the earphone 40 (model TMG-ACD) was also measured by the ER-7 probe tube measurement with the eartip snuggly inserted in a SILICONE® rubber ear model, with one probe placed inside the ear model and the other outside to measure the deferential sound pressure level across the earphone in the ear model. The resultant attenuation of the earphone eartip was tabulated in Row-B.

Row C shows the maximum allowable noise level in ⅓ octave bands for audiometric testing of threshold levels according to ANSI 3.1 in the condition of ears not covered. Row-D estimates the permissible noise level for each frequency band according to the teachings of the present invention, with a presentation level 30 dB above normal threshold of hearing levels. The permissible level for present method was estimated by adding 30 dB to the permissible noise levels according to the ANSI standard for threshold testing, and the attenuation of the earphone eartip occluding the ear.

Accordingly, the permissible noise level (D) can be calculated from the equation:

Earphone Attenuation(B)+Allowed noise level per ANSI(C)+30 dB

TABLE 1

|  | Frequency in Hz. | | | | |
| --- | --- | --- | --- | --- | --- |
|  | 500 Hz | 1000 Hz | 2000 Hz | 4000 Hz | 6000 Hz |
| A—Room Noise in dB SPL | 30.0 | 29.5 | 30.1 | 32.0 | 33.3 |
| B—Earphone Attenuation in dB | 9.8 | 13.3 | 18.9 | 4.8 | 9.1 |
| C—Allowed Noise dB SPL per ANSI | 11 | 8 | 9 | 6 | 8 |
| D—Permissible Noise in dB SPL (est.) | 50.8 | 51.3 | 57.9 | 40.8 | 47.1 |
| E—Estimated Noise Margin in dB SPL | 20.8 | 21.8 | 27.8 | 8.8 | 13.8 |

ANALYSIS AND CONCLUSION FOR EXPERIMENT

Testing the hearing ability at or above 30 dB HL across the audiometric frequency range of 500 to 6000 Hz. is possible in reasonably quiet environments such as an office, even in the presence of computers and other instruments using the principles of the present invention. There was a substantial margin of noise at virtually all test frequencies, with the exception of 4,000 Hz having only an 8.8 dB margin. This is possible due to relatively poor sound attenuation of the eartip at this particular frequency. It should be understood that noise levels are expected to vary considerably across room environments due to room acoustics, noise sources, distance and the position of the consumer with respect to noise sources. However, these variations are expected to be substantially mitigated by testing at suprathreshold levels above 20 dB, and particularly at 30 dB HL as in this example.

Asymmetric hearing losses represent a challenge to hearing assessment, whereby masking sounds may be required for the non-test ear. Masking is a task not easily understood or implemented by a lay person. However, the system and methods disclosed herein are well suited to automatically introduce masking sounds to the non-test ear in order to mitigate cross-over errors in asymmetrical hearing losses. For example, by automatically delivering a narrow band, or broad band noise to the non-test ear. In the example embodiments, test sounds are presented at frequencies of 500, 1000, 2000, 4000 & 6000 Hz, preferably with at least one natural sound as disclosed above. Test signals may also be tonal such as warble tones, mixed tones, or band-limited noise. Pure tones may also be presented but are generally considered less desirable. Masking of a non-test ear using a stimulus of predetermined level may also mitigate the adverse effects of room noise, for example by presenting a masking noise to the test ear to compete and override ambient noise.

The following method and computation formula represents an example for computing a hearing profile score (HPS). A scoring scale from 0 to 5 is assigned for each test levels from 30 to 80 dB HL (Table 2), incrementing by 10 dB, for 5 test frequencies of 500, 1000, 2000, 4000 and 6000 Hz. The hearing profile score is then computed according to the minimum audible level (MAL) values according to weighting factors from the Speech Intelligibility Index per ANSI S3.5-1997: "Methods for Calculation of the Speech Intelligibility Index". The weighting factor for 250 Hz. was added to the value for 500 Hz weighting since hearing losses at these adjacent frequency bands is generally similar for the hearing loss population of interest, and since there is no testing at the frequency of 250 Hz in the example embodiment. The weighting factor for 8000 Hz was substituted for 6000 Hz, also since no testing occurs at 8000 Hz in this example. In other examples, testing at 8,000 Hz may be included.

TABLE 2

|  | Presentation Level | | | | | |
| --- | --- | --- | --- | --- | --- | --- |
|  | 80 HL | 70 HL | 60 HL | 50 HL | 40 HL | 30 HL |
| Scoring Factor | 0 | 1 | 2 | 3 | 4 | 5 |

The hearing profile score is then computed by adding weighted scores for all frequency bands, and scaling if necessary to yield the maximum index level employed, being 5 in this case. The fractional hearing profile score 90 (FIG. 13) in the example tabulated below is 3.17 out of 5, which may be presented as the hearing profile score 71 of 3 when rounded to the nearest whole digit.

TABLE 3

|  | Test Frequency Band | | | | |
| --- | --- | --- | --- | --- | --- |
|  | 500 Hz | 1000 Hz | 2000 Hz | 4000 Hz | 6000 |
| A. Example Minimum Audible Level | 40 HL | 40 HL | 50 HL | 60 HL | 70 HL |
| B. Scoring Factor | 4 | 4 | 3 | 2 | 1 |
| C. Band Importance Weighting* | .23 | .24 | .26 | .21 | .06 |
| D. Hearing Profile Score per frequency | .92 | .96 | .81 | .42 | .06 |
| E. Hearing Profile Score | 3.17/5 or 3/5 if rounded | | | | |

*per ANSI S3.5-1997

Although examples of the invention have been described herein, variations and modifications of this exemplary embodiment and method may be made without departing from the true spirit and scope of the invention. Thus, the above-described embodiments of the invention should not be viewed as exhaustive or as limiting the invention to the precise configurations or techniques disclosed. Rather, it is intended that the invention shall be limited only by the appended claims and the rules and principles of applicable law.

What is claimed is:

1. A method of administering a hearing evaluation for a consumer, the method comprising:
   generating test audio signals at predetermined levels by an audio generator;
   delivering a sequence of calibrated acoustic test stimuli, representing the test audio signals, in each of three or more test frequency bands within an audiometric frequency range, to the ear of the consumer at suprathreshold sound levels of at least 20 dB HL, and wherein a step level for consecutive calibrated test stimuli at each test frequency band is at least 10 dB;
   registering, using a computerized hearing test system, minimum audibility levels of the consumer within the suprathreshold sound levels delivered at each test frequency band; and
   presenting a computed hearing profile score to the consumer by the computerized hearing test system, wherein the computed hearing profile score is based on the consumer's minimum audibility level only within the suprathreshold sound levels delivered at or above 20 dB HL in step sizes of at least 10 dB at each test frequency band.

2. The method of claim 1, wherein the computerized hearing test system comprises a personal computer.

3. The method of claim 2, wherein the personal computer is selected from the group consisting of a smart phone and a tablet.

4. The method of claim 2, further comprising providing online customer support to the consumer by a remote customer support computer system with connection to the personal computer via the Internet.

5. The method of claim 4, wherein the online customer support comprises streaming customer support audio to the personal computer from the customer support computer system.

6. The method of claim 2, wherein the hearing profile score is presented through a display of the personal computer.

7. The method of claim 1, wherein the hearing test system comprises an earphone configured to deliver the calibrated acoustic test stimuli to an ear of the consumer.

8. The method of claim 7, wherein the earphone is configured to attenuate ambient background noise by at least 5 dB across the audiometric frequency range of 500 to 6,000 Hz.

9. The method of claim 7, wherein the earphone comprises an ear canal insert configured to occlude the ear canal and attenuate ambient background noise.

10. The method of claim 1, wherein a maximum of the computed heating profile score is between four and six.

11. The method of claim 1, wherein the computerized hearing test system is connected online to any of a remote server and a remote database.

12. The method of claim 1, wherein the remote server hosts a hearing profile software application configured to administer the hearing evaluation for the consumer.

13. The method of claim 12, further comprising executing the hearing profile software application from a personal computer.

14. The method of claim 1, further comprising saving the hearing profile score at a remote database.

15. The method of claim 1, wherein the calibrated acoustic test stimuli include a chirp sound representing a relatively high frequency test stimulus.

16. The method of claim 1, wherein the calibrated acoustic test stimuli include a drum sound representing a relatively low frequency test stimulus.

17. The method of claim 1, wherein the calibrated acoustic test stimuli include at least one natural sound.

18. The method of claim 17, wherein the natural sound is a recording processed to limit content within a test frequency band.

19. The method of claim 1, wherein the hearing profile score is computed at least partially on the basis of a speech articulation index.

20. The method of claim 1, further comprising presenting hearing aid candidacy to the consumer, wherein the hearing aid candidacy is at least partially based on the hearing profile score.

21. The method of claim 1, further comprising determining an ambient sound level.

22. The method of claim 21, wherein a microphone associated with the computerized hearing test system is used to determine the ambient sound level.

23. The method of claim 1, further comprising streaming the consumer's speech to a customer support computer system via the Internet.

24. The method of claim 1, wherein a minimum suprathreshold sound level presented is approximately 30 dB HL.

25. The method of claim 1, further comprising producing masking sound to a non-test ear.

26. A method of administering a hearing profile test, the method comprising:
   presenting a sequence of acoustic test stimuli in each of three or more test frequency bands within an audiometric frequency range at suprathreshold sound levels of at least 20 dB HL by a computerized hearing test system, wherein at least one of the acoustic test stimuli represents a non-tonal natural sound;
   presenting the sequence of acoustic test stimuli at a step level of at least 10 dB at each test frequency band;
   registering a consumer's minimal audibility level within the suprathreshold sound levels presented at each test frequency band, and
   presenting to the consumer a hearing profile score computed based on the minimum audibility level only within the suprathreshold sound levels presented at or above 20 dB HL in step sizes of at least 10 dB at each test frequency band.

27. A method of determining a hearing aid candidacy of a consumer by a hearing test system; the method comprising:
   applying an earphone to the consumer's ear, wherein the earphone is configured to attenuate ambient background noise;
   presenting a sequence of calibrated test acoustic stimuli to the ear with the earphone at suprathreshold levels of at least 20 dB I-IL in each of multiple test frequency bands;
   registering a minimum audibility level within the suprathreshold sound levels presented to the consumer at each test frequency band;
   presenting to the consumer a hearing profile score computed based on the minimum audibility level only within the suprathreshold sound levels presented at or above 20 dB HL at each test frequency band; and
   indicating hearing aid candidacy to the consumer, based at least in part on the hearing profile score.

28. A method of online hearing assessment of a consumer, the method comprising:
   executing a hearing assessment application by a personal computer, wherein the hearing assessment application communicatively coupled to a remote server;

delivering test audio signals to an earphone from an audio generator communicatively coupled to the personal computer;

delivering a sequence of calibrated acoustic output signals from the earphone at suprathreshold sound levels of at least 20 dB HL, and step level increments of at least 10 dB in each of three or more test frequency bands within an audiometric frequency range;

registering, by the personal computer, the consumer's minimum audibility level within the suprathreshold sound levels delivered at each of the test frequency bands; and presenting to the consumer a computed hearing profile score based on the consumer's minimal audibility level only within the suprathreshold sound levels delivered at or above 20 dB HL in step sizes of at least 10 dB at each test frequency band.

29. A hearing profile test system, comprising;

an earphone configured to receive test audio signals to produce a sequence of calibrated acoustic test stimuli in each of three or more test frequency bands within an audiometric frequency range to the ear at suprathreshold sound levels of at least 20 dB HL, and step levels of at least 10 dB at each test frequency band, wherein said earphone is configured to occlude the ear canal and attenuate ambient background sound;

a handheld device incorporating an audio signal generator configured to produce the test audio signals; and a personal computer communicatively coupled to the handheld device, the personal computer configured to execute a hearing profile test application and to present a computed hearing profile score based on a consumer's minimum audibility level only within the suprathreshold sound levels at or above 20 dB HL in step sizes of at least 10 dB produced at each test frequency band.

30. The hearing profile test system of claim 29, further comprising a microphone configured to sense sound in a vicinity of the consumer.

31. The hearing profile test system of claim 30, wherein the microphone is configured to relay consumer speech to a customer support personnel located remotely.

32. The hearing profile test system of claim 29, wherein the handheld device is connected to the personal computer by a USB connection.

33. The hearing profile test system of claim 29, wherein the personal computer is selected from the group consisting of a smart phone and a tablet computer.

34. The hearing profile test system of claim 29, wherein the personal computer is configured to receive any of audio and instructions from a customer support computer remotely located.

35. A system for online hearing evaluation, the system comprising;

a handheld device including an audio signal generator configured to produce audio signal outputs;

an earphone configured to receive the audio signal output from the handheld device and to deliver a sequence of calibrated acoustic test stimuli to a consumer's ear at suprathreshold sound levels of at least 20 dB HL in each of three or more test frequency bands within an audiometric frequency range, wherein a step level between consecutive calibrated test stimuli at each test frequency band is at least 10 dB; and a personal computer communicatively coupled to the handheld device and to a remote server, wherein the personal computer is configured to execute a hearing evaluation application connected to a remote server and display a computed hearing profile score, wherein the hearing evaluation application is configured to register minimum audibility levels of the consumer in response to the suprathreshold sound level presentations and to compute the hearing profile score based on the consumer's minimum audibility level only within the suprathreshold sound levels delivered at or above 20 dB HL in step sizes of at least 10 dB at each test frequency band.

36. The system of claim 35, further comprising a microphone.

37. The system of claim 35, wherein the personal computer is configured to relay speech to a remote customer support computer system via the Internet.

38. The system of claim 35, further comprising a customer support computer system configured to relay any of audio and instructions to the personal computer via the Internet.

* * * * *